United States Patent
Sydor

[11] Patent Number: 5,148,549
[45] Date of Patent: Sep. 22, 1992

[54] BACK SUPPORT WITH SIDE OPENINGS AND ATTACHED APRON

[75] Inventor: Robin M. Sydor, Robbinsdale, Minn.

[73] Assignee: Ergodyne Corporation, St. Paul, Minn.

[21] Appl. No.: 689,980

[22] Filed: Apr. 23, 1991

[51] Int. Cl.⁵ .................... A41D 13/04; A61F 5/02
[52] U.S. Cl. ................................................. 2/44; 2/48; 2/51; 2/310; 2/311; 2/312; 128/95.1; 128/845; 128/875; 128/876; 602/19
[58] Field of Search ............... 2/44, 46, 48, 50, 51, 2/92, 102, 310, 311, 312, 313, 314, 315, 316, 317, 338; 450/1, 15, 16, 22, 155; 128/78, 95.1, 99.1, 100.1, 101.1, 869, 845, 875, 876

[56] References Cited

U.S. PATENT DOCUMENTS

| | | | |
|---|---|---|---|
| 472,086 | 4/1892 | Town | 2/44 |
| 572,465 | 12/1896 | Woolfolk et al. | 450/155 |
| 657,133 | 9/1900 | Redick | 450/15 |
| 811,167 | 1/1906 | Paddock | 2/92 |
| 933,610 | 9/1909 | Yanowsky | 450/15 |
| 934,625 | 9/1909 | Petrel | 450/155 X |
| 1,006,862 | 10/1911 | McCormick | 450/155 X |
| 1,006,863 | 10/1911 | McCormick | 450/155 X |
| 1,565,808 | 12/1925 | Levy | 450/155 X |
| 1,983,636 | 12/1934 | Palkens | 450/155 X |
| 2,104,699 | 1/1938 | O'Dell | 128/78 |
| 2,840,822 | 7/1958 | Ericsson | 450/155 X |
| 3,116,735 | 1/1964 | Geimer | 2/44 X |
| 3,554,190 | 1/1971 | Kaplan | 2/44 X |
| 4,782,535 | 11/1988 | Yewer, Jr. et al. | 2/321 X |
| 4,866,789 | 9/1989 | Dorm | 2/92 X |
| 4,981,307 | 1/1991 | Walsh | 2/44 X |
| 5,007,412 | 4/1991 | DeWall | 2/44 X |
| 5,040,524 | 8/1991 | Votel et al. | 128/95.1 X |

FOREIGN PATENT DOCUMENTS 0055238  6/1982  European Pat. Off. ............... 2/92

OTHER PUBLICATIONS

*CompVest Back Support* Brochure, 1984 of Comp Equipment Corporation (now known as Ergodyne Corporation).

Primary Examiner—Werner H. Schroeder
Assistant Examiner—Jeanette E. Chapman
Attorney, Agent, or Firm—Merchant, Gould, Smith, Edell, Welter & Schmidt

[57] ABSTRACT

A back support (10) for providing abdominal and lumbosacral support has a waistband (11) comprising a front panel (12) and a second panel (13). An elastic band (50) is operatively connected to the waistband (11). An apron member (40) is operatively connected to the top portion of the front panel (12). A pocket member (60) is operatively connected to the bottom portion of the front panel (12).

10 Claims, 2 Drawing Sheets

BACK SUPPORT WITH SIDE OPENINGS AND ATTACHED APRON

BACKGROUND OF THE INVENTION

1. Field of the Invention

This invention relates generally to back supports and more particularly to a back support designed to not only prevent riding up of the support when worn, but also having an apron, utility pockets and separate front and second panels, thereby allowing side entry to the back support.

2. Description of the Prior Art

The present invention is for use by persons who do relatively heavy or awkward lifting, pulling or pushing, and is primarily to help prevent serious back injury by providing abdominal and lumbosacral support. It is not intended to be a therapeutic device for persons who have previous back problems or abdominal muscle injury, although it can be used to help prevent the reoccurrence of such problems. The invention is particularly useful in hospitals or nursing homes by nurses or orderlies or the like who, from time to time, might have to lift or pull up patients or residents and need some support to prevent back problems from occurring, yet during the normal course of their other daily activities, they do not need this aid. They have the need for this type of support device occasionally, so want it handy as the need arises, and also need to be comfortable while wearing the device when not needed for support. Similar applications are to be found for industry use and for workers in other trades and industries. Specifically, the present invention can readily be adapted for use by workers which need not only the benefit of the prevention of back injury, but also need a protective apron to protect either themselves or their clothing and also need pockets. The pockets in the regular clothing worn by the worker are typically covered up by the support. There are a number of stress band type devices which have been used over the years as therapeutic devices for helping to cure various aches and pains due to muscle or other type of damage, and particularly with respect to back problems. Many of these earlier devices are constructed so that they can not be conveniently removed or unfastened and then re-fastened from time to time as the need for the added support comes and goes. In other words, they must be worn full-time or not at all. Still others are bulky and/or cumbersome and/or fairly heavy and if used or worn as an outer garment, interfere with the normal working activities of the users. Other problems with the prior art involve complications in hook up and adjustment, cleaning and not being universal for different sizes and shapes.

For the past several years, the assignee of the present application, Ergodyne Corporation, has sold a back support which has addressed and solved many of the above-noted problems. The support is easy to use, adjustable for many different sizes, easily cleaned, and does not interfere with normal activity. It can readily be temporarily tightened for support when needed and released when normal activities occur.

While the above-mentioned back support has found great popularity and has provided for a much improved product, there are still several areas of concern relating not only to the assignee's back support but others presently available.

When such back supports have been worn by females, the support has tended to ride up on the female during use. While this has not been solely a problem for females, it has been typically been more of a problem for females due to the size of a female's hips in relationship to her waist. Typically, the hips tend to be larger in relationship to their waist. While this is of course not only a characteristic of females, females do tend to have this body shape more often than men. Accordingly, when used throughout this application, reference to females will not be limited to only females, but to persons having the more typical female body shape with respect to the hips in relationship to the waist. Also, depending on the activity engaged in by the wearer, a male may also have his support ride up while in use.

In addition, the elastic band of the back support has typically been secured by means which would not readily release the elastic band. Therefore, when an elastic band was faulty, it was necessary to replace the whole back support. In addition, it has been quite popular to now have a logo or other writing on the elastic band as that is what is visible. When ordered by different companies, they will quite often want their own logo on the elastic band. By previous methods of construction, it was necessary to keep in stock the combination of waistband and elastic band. Applicants have found by having the elastic band removable, the same waistband may be used by many elastic bands having various logos.

Still further, the back supports to date, while comfortable, have tended to be made of a textile material, and have not had efficient transfer of heat and moisture from the wearer of the back support. Still further, for industrial workers using tools, which are normally carried on a tool belt, back supports have not been popular as there have been the necessity of not only wearing a tool belt, but also the back support. This has proved cumbersome and the workers have tended not to wear both. U.S. Pat. No. 4,782,535 does show a belt, typically worn by weight lifters, which has been adapted to hold tools. However, the tools are supported directly from the strap webbing. The back support disclosed in pending application U.S. Ser. No. 07/516,323, filed Apr. 30, 1990, and entitled "BACK SUPPORT", addresses many of these problems, there are still several concerns which need to be addressed. When a person is wearing the support, the pockets in the worker's clothing are typically covered. Therefore, there is no readily available pocket in which to place various items. Still further, the supports are often worn by nurses or workers that need to protect the clothing which they have on underneath the support. Finally, a few of the wearers have some problems with the single point of entry into the back support.

The present invention addresses the problems associated with the prior art devices.

SUMMARY OF THE INVENTION

The present invention is a back support for providing abdominal and lumbosacral support as needed by the wearer. The back support includes a waistband of a construction having a limited amount of stretch. The waistband includes a front panel having first and second ends and inner and outer surfaces. The waistband further includes a second panel having first and second ends and inner and outer surfaces. The support also includes a means for suspending, from a wearer's shoulder, the front panel proximate the wearer's front and the second panel proximate the wearer's back. Further, there is a means for operatively connecting, after suspending from the wearer's shoulders, the first end of the front panel to the first end of the second panel and operatively connecting the second end of the front panel to the second end of the side panel. An elastic band is operatively connected to the outer surfaces of the first and second panels. The elastic band has first and second ends releasably connected to the outer surface of the front panel, so as to be easily moved between an unstretched and a stretched position.

In a preferred embodiment, loop material and hook material are used to operatively connect the front and second panels. Still further, the loop and hook materials are utilized to connect the elastic band to the front panel.

In a preferred embodiment, the support also includes an apron panel operatively connected to the front panel and positioned above the front panel and still further a pocket panel operatively connected to the front panel and positioned below the front panel.

DETAILED DESCRIPTION OF THE PREFERRED EMBODIMENT

Figure 1:
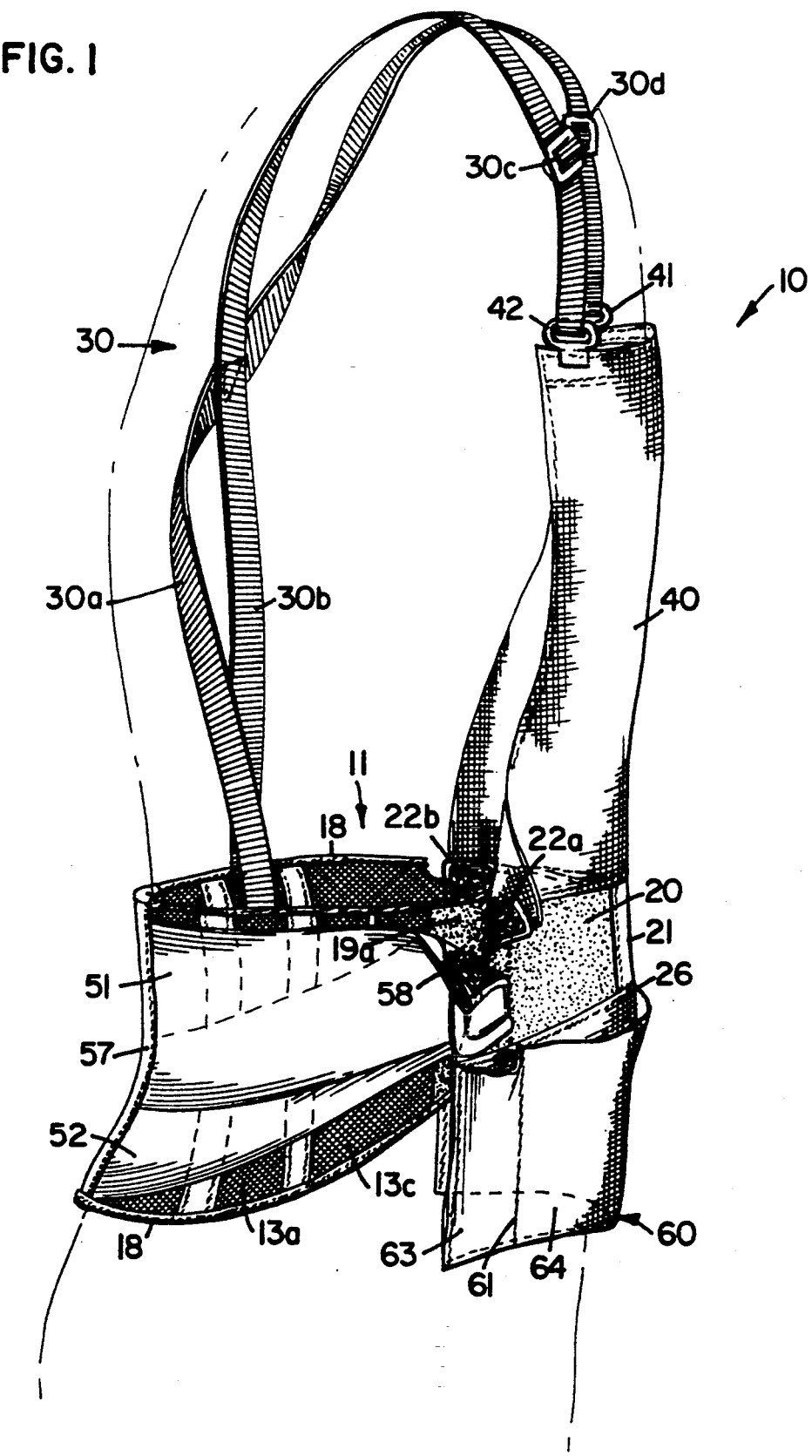
FIG. 1 is a perspective view of the back support of the present invention with a portion of the wearer being shown in phantom.

Referring to the drawings, wherein like numerals represent like parts throughout the several views, there is generally disclosed at 10 a back support. The back support 10 includes a waistband 11 having a front panel 12 and a second panel 13. While the combination of the front panel 12 and second panel 13 is referred to as a waistband, it is understood that the waistband 11 is designed to rest below the navel and accordingly, is not defined as being literally a band around the waist, but also may be below the waist. A piece of fabric is cut to the size of the second panel 13 and front panel 12. Depending upon the embodiment of the invention to be constructed, the fabric may be of either a stretchable or unstretchable fabric. As will be discussed more fully hereafter, in one embodiment it is desired to have some stretchability to the waistband 11, while in other embodiments, such as when heavy objects are to be positioned in the pockets, it is desirable to not have any stretch to the waistband 11. If stretchable materials are desired, a suitable material, such as Spandex ®, may be utilized. If it is desired to be non-stretchable, any suitable material, such as Apex, may be utilized. A plurality of semi-rigid stays 15 are secured to the second panel 13. On the inside of the second panel 13, next to the wearer, the stays 15 are covered by a rubberized elastic fabric and on the outside by a vinyl fabric. As shown in FIG. 1, two stays 15 are utilized on each half of the second panel 13. The stays 15 are inserted between the rubberized elastic fabric and the inner surface of the second panel 13. The vinyl fabric is attached to the outside of the second panel 13 over the area where the stays 15 are located. A ribbing or binding 18 is stitched across the top and bottom of the entire second panel 13. Loop fabrics 19a and 19b are stitched to the outside of the right and left of the second panel 13.

Figure 2:
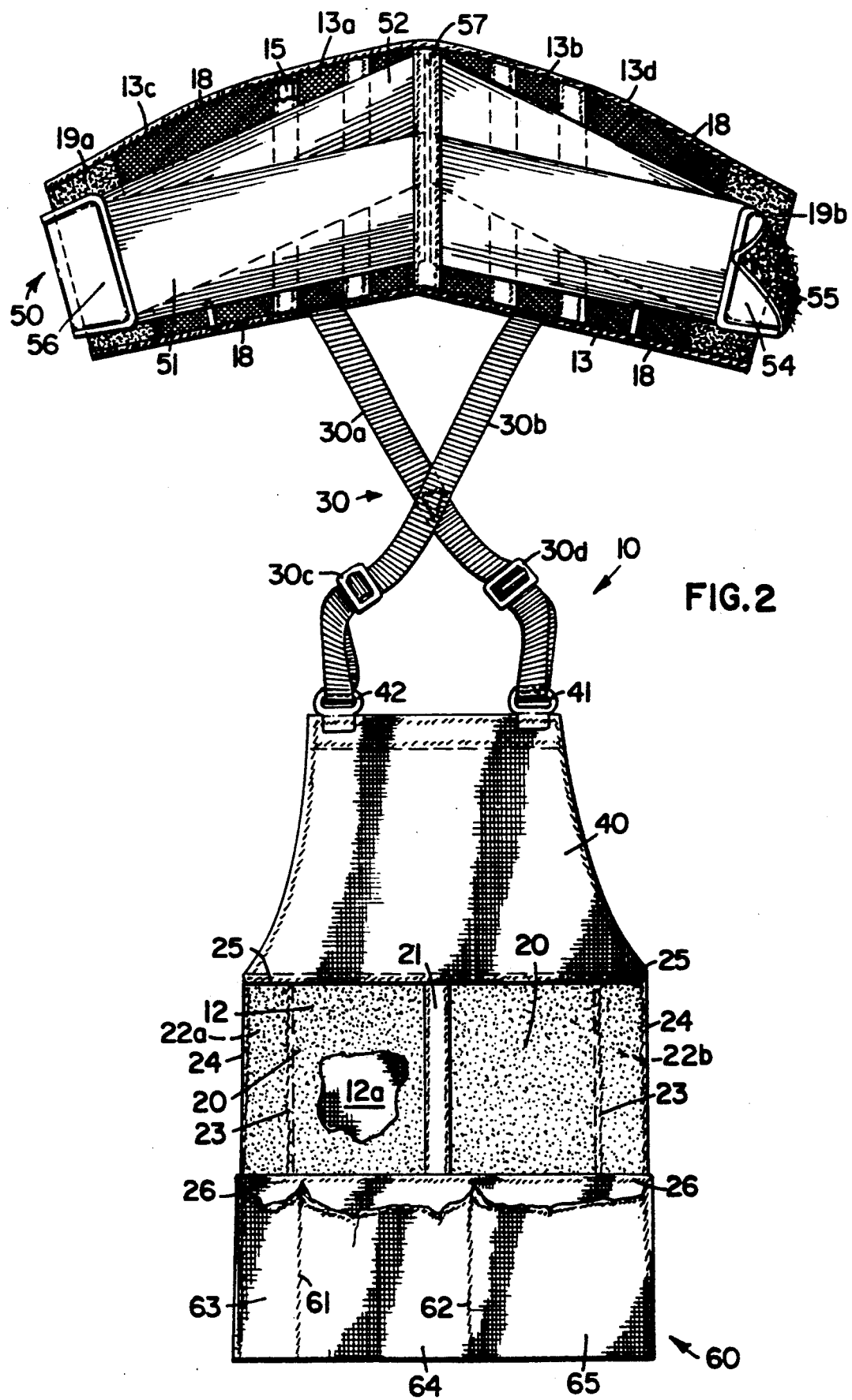
FIG. 2 is a plan view of the support shown in FIG. 1 showing the top surface of the support, with the support being positioned in a generally horizontal plane.

The front panel 12 is generally rectangular in shape and is constructed from a fabric 12a similar to the fabric used to construct the second panel 13. On the outside surface of the front panel 12, a loop fabric 20 is stitched. A vinyl member 21 is vertically stitched between each half of the front panel 12. The vinyl member is used to cover the stitching between each half of the panel 12. Alternately, only a single piece of fabric 20 may be used, thereby eliminating the need for vinyl member 21. On the inside of the front panel 12, rectangular shaped pieces of hook material 22a and 22b are stitched, on the right and left sides respectively, to the underneath side of the front panel 12. The stitching 23, 24, 25 and 26, which stitches the material 22a and 22b to the panel 12, is best seen in FIG. 2 and generally defines a rectangle. The hook materials 22a and 22b and loop fabrics 19a, 19b and 20 may be of any type well known in the industry which would form a hook and loop type fastener such as Velcro ® brand. The fabric utilized to construct the front panel 12 and second panel 13 may be somewhat stretchable, however, the loop fabrics 19a, 19b and 20 are substantially non-stretchable. The fabric for the front and second panels may be any suitable material such as a stretchable Spandex ® material. The binding 18 may be made of a suitable material such as tricot. A previously stated, if a stretchable material such as Spandex ® is utilized, the overall waistband will have some stretchability. For instance, with a waistband 11 having an overall length of approximately 42 inches, the waistband 11 may expand from one half to three inches and preferably from one and one half to two inches. This allows the waistband 11 to have the capabilities of stretching and conforming to the body of the wearer.

The second panel 13 has a right half 13a and a left half 13b. The right half has a bottom edge 13c and the left half has a bottom edge 13d. As can be seen in the drawings, the right half 13a and the left half 13b form a generally V-shaped second panel 13. Adjustable suspenders, generally designated as 30, are secured to the top edge of the second panel 13 at one end and to the top edge of the apron member 40 at their other end. The suspenders 30 include a first strap 30a and a second strap 30b. Two loop members 41 and 42 are stitched to the top of the apron 40 and one of the straps 30a and 30b positioned through the loops 41 and 42 respectively. Adjustable buckles 30c and 30d are operatively connected to the straps 30a and 30b, thereby allowing the length of the straps to be adjusted. It is of course understood that other suitable means of similarly connecting the front panel 12 to the second panel 13 may be utilized.

A four inch wide elastic band, generally designated as 50, has a top four inch band 51 and a bottom four inch band 52. The top band 51 is generally rectangular but has a slight V shape and the bottom band 52 has more of a V shape. The bands 51 and 52 are connected to each other at their ends by suitable means such as stitching. The left ends of the bands 51 and 52 have a vinyl piece 54 positioned on the outside surface and a hook material 55 fastened on the bottom surface. Similarly, the right ends are connected and have a vinyl piece 56 on the outside surface and a hoop material 58 underneath. The bands 51 and 52 are held in place, proximate their middle, to the second panel 13 by a rectangular fabric piece 57 which is stitched to the second panel 13. The bands 51 and 52 are positioned between the fabric 57 and the panel 13. Alternative embodiments of similarly connecting the elastic bands 51 and 52 to the panel 13 may be utilized, such as those disclosed in U.S. Ser. No.

07/516,323, filed Apr. 30, 1990, and is hereby incorporated by reference. Each of the bands 51 and 52 may be of any suitable length, such as approximately 24 inches when not stretched. When stretched, this length may be increased to a suitable length so as to provide the necessary support. While the specific design of the support will dictate the length of the stretch desired, it has been found that from 5 to 15 inches and preferably from about 9 to 13and still more preferably 10 to 12 inches of stretch is desirable.

An apron portion 40 is operatively connected, such as by stitching, to the top of the front panel 12. Since the front panel 12 is positioned proximate the waist, the apron 40 would cover the upper body portion of the wearer. If made from a cloth type material, the apron 40 would protect the wearer from liquid spills, as well as dirt and grease. The apron 40 could also be made from a variety of specialized material to form a special protective barrier to protect the wearer.

A pocket member 60 is operatively connected to the bottom of the front panel 12, by suitable means such as stitching. A piece of fabric may simply be folded upward and then stitched along two seams 61 and 62 to form three open top pockets 63, 64 and 65. Of course, it is understood that other suitable means may be utilized to form pocket members which would depend from the lower portion of the front panel 12.

It has further been found that it is sometimes desirable to have the front panel 12, pocket member 60 and apron member 40 disposable. The pocket member 60 may tend to wear out after use and the apron member 40 may tend to become soiled. The second panel 13 and elastic band 50 tend not to wear out as quickly. Accordingly, it would be advantageous to have the entire front portion replaceable or disposable. One convenient way of doing so would be to have the loops 41 and 42 clipped onto the apron member 40 instead of being stitched. Then, the loop members 41 and 42 could simply be unclipped and a new front portion (pocket member 60, front panel 12 and apron member 40) clipped to the loop members 41 and 42.

In operation, the wearer places the suspenders 30 over her shoulders so that the right side 13a is on her right side and the left side 13b is on her left side. When the suspenders are placed over the wearer's head, the front panel 12 is not attached to the second panel 13. That is, the support 10 is separated, as shown in FIG. 2. When putting the suspenders 30 over her shoulders, the elastic band 50 typically will have its hook materials 55 and 58 secured to the loop materials 19a and 19b so that the band 50 would appear as in FIG. 2, without having the end 55 turned up. Then, the wearer would release the ends of the elastic band 50 from the loop materials 19a and 19b. The right side 13awould then be pulled toward the right side of the front panel 12 and the hook material 22a would be placed on top of the loop material 19a. Then, the left side 13b would be brought toward the left side of the front panel 12 and the hook material 22b is then placed on top of the loop material 19b,thereby operatively connecting the front panel 12 to the second panel 13. Then, the wearer grasps each end of the elastic band 50 by grasping each end of the vinyl tabs 54 and 56 and stretches the elastic band slightly so that the hook material 55 and 58 contacts the loop material 20.

The wearer then continues to wear the back support with the elastic band 50 having its ends attached to the loop material 20 in a substantially unstretched state. Alternately, the ends could be allowed to hang loose. Then, just before lifting, the ends of the elastic band 50 are grabbed at the vinyl tabs 54 and 56 and stretched as far forward as possible, and then placed against the fabric 20 so that the hook material 58 on the right side and the hook material 55 on the left side fastens the elastic band 50 in a stretched position. FIG. 1 shows the support 10 on a wearer. The V-shaped waistband is able to be worn by the wearer without having the support ride up as the wearer continues to wear the support 10.

The apron member 40 provides for needed protection in various industries, such as the health care industry where the wearer's clothing may become damaged or soiled. The apron will protect the wearer's clothing from splashes and/or dirt and other contaminants.

Still further, the support 10 has a pocket member 60 which allows for the wearer to have access to pockets. With the prior art devices, the support 10 would typically cover up the pockets on the normal clothing of the wearer. The pocket member 60 provides pockets which are quite often necessary for the wearer, especially in the health care industry.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follow in the spirit and broad scope of the appended claims are included.

We claim:

1. A back support for providing abdominal and lumbosacral support as needed by the wearer, comprising:
    (a) a waistband of a construction having a limited amount of stretch, said waistband comprising:
        (i) a front panel having first and second ends and inner and outer surfaces;
        (ii) a second panel having first and second ends and inner and outer surfaces;
        (iii) means for suspending, from a wearer's shoulders, said front panel proximate the wearer's front said second panel proximate said wearer's back; and
        (iv) means for operatively connecting, after suspending from the wearer's shoulders, said first end of said front panel to said first end of said second panel and for operatively connecting said second end of said front panel to said second end of said second panel; and
    (b) an elastic band operatively connected to said outer surfaces of said front and second panels, said elastic band having first and second ends releasably connected to said outer surface of said front panel, so as to be easily moved between an unstretched and a stretched position.

2. The support of claim 1, wherein said suspending means comprises suspenders, said suspenders having first and second straps each having first and second ends, said first ends operatively connected to said front panel and said second ends operatively connected to said second panel.

3. The support of claim 2, wherein said straps have an adjustable length.

4. The support of claim 1, wherein said connecting means comprises hook material and loop material operatively connected to said front and second panels.

5. The support of claim 4, wherein said elastic band is operatively connected to said front panel with hook material and loop material.

6. The support of claim 5, further comprising:
(a) first hook material operatively connected to said inside surface of said front panel proximate both first and second ends; and
(b) first loop material operatively connected to said outside surface of said second panel proximate both first and second ends, said first hook material positioned to be engaged by said first hook material.

7. The support of claim 6, further comprising:
(a) said elastic band having an inside surface, outside surface, first end and second end;
(b) second loop material operatively connected to said outside surface of said front panel, said second loop material covering substantially all of said outside surface; and
(c) second hook material operatively connected to said inside surface of said elastic band proximate both first an second ends.

8. The support of claim 1, further comprising an apron panel operatively connected to said front panel and positioned above said front panel.

9. The support of claim 8, further comprising a pocket panel operatively connected to said front panel and positioned below said front panel.

10. A back support for providing abdominal and lumbosacral support as needed by the wearer, comprising:
(a) a waistband of a construction having a limited amount of stretch, said waistband comprising:
  (i) a front panel having first and second ends and inner and outer surfaces;
  (ii) a second panel having first and second ends and inner and outer surfaces;
  (iii) means for suspending, from a wearer's shoulders, said front panel proximate the wearer's front said second panel proximate said wearer's back; and
  (iv) means for operatively connecting, after suspending from the wearer's shoulders, said first end of said front panel to said first end of said second panel and for operatively connecting said second end of said front panel to said second end of said second panel; and
(b) an elastic band operatively connected to said outer surfaces of said front and second panels, said elastic band having first and second ends releaseably connected to said outer surface of said front panel, so as to be easily moved between an unstretched and a stretched position;
(c) first hook material operatively connected to said inside surface of said front panel proximate both first and second ends;
(d) first loop material operatively connected to said outside surface of said second panel proximate both first and second ends, said first hook material positioned to be engaged by said first loop material;
(e) said elastic band having an inside surface, outside surface, first end and second end;
(f) second loop material operatively connected to said outside surface of said front panel, said second loop material covering substantially all of said outside surface;
(g) second hook material operatively connected to said inside surface of said elastic band proximate both first an second ends;
(h) an apron panel operatively connected to said front panel and positioned above said front panel; and
(i) a pocket panel operatively connected to said front panel and positioned below said front panel.

* * * * *